United States Patent [19]

Pilgram

[11] 4,439,226
[45] Mar. 27, 1984

[54] HERBICIDAL 4-((BENZIMIDAZOL-1-YL)PHENOXY)AL-KANOIC ACIDS, ESTERS AND SALTS

[75] Inventor: Kurt H. Pilgram, Modesto, Calif.

[73] Assignee: Shell Oil Company, Houston, Tex.

[21] Appl. No.: 419,865

[22] Filed: Sep. 20, 1982

[51] Int. Cl.$^3$ .................. A01N 43/52; C07D 235/08
[52] U.S. Cl. ........................................ 71/92; 548/325; 560/45
[58] Field of Search .......................... 548/325; 71/92

[56] References Cited

U.S. PATENT DOCUMENTS 3,574,218 4/1971 Hideg et al. .................. 548/325 X
3,804,839 4/1974 Dahm et al. .................. 548/325 X Primary Examiner—Richard A. Schwartz

[57] ABSTRACT

Certain 4-((benzimidazol-1-yl)phenoxy)alkanoic acids, esters and salts, useful as herbicides.

6 Claims, No Drawings

HERBICIDAL 4-((BENZIMIDAZOL-1-YL)PHENOXY)ALKANOIC ACIDS, ESTERS AND SALTS

DESCRIPTION OF THE INVENTION

It has been found that certain 4-(benzimidazol-1-yl)phenoxy)alkanoic acids, esters and salts adversely affect the growth of plants to which they are applied, and thus are of interest for controlling the growth of unwanted plants. These compounds are described by the formula:

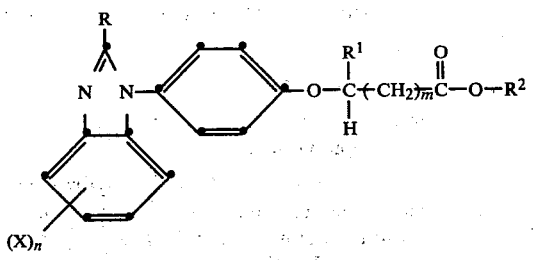

wherein n is 1 and X is trifluoromethyl, R is hydrogen, methyl or ethyl; $R^1$ is methyl, ethyl or methoxymethyl; m is 0, 1 or 2; and $R^2$ is hydrogen, alkyl of from one to four carbon atoms, and when $R^2$ is hydrogen, the alkali metal and ammonium $(N(R^3)_3)$ salts, wherein each $R^3$ is hydrogen or alkyl of from one to six carbon atoms.

Highest phytotoxicity appears to reside in the subclass of the class defined in Formula I wherein the trifluoromethyl moiety is bonded to the ring at the 5-position, R and $R^1$ each represents methyl, m is 0, and $R^2$ represents hydrogen, methyl or ethyl, so that this subclass forms a preferred aspect of the invention.

The compounds of Formula I are prepared by treating an ester of the formula

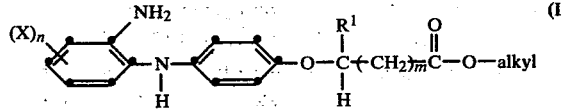

with a trialkyl ester of an orthoalkane acid, such as triethyl orthoformate (R=H), orthoacetate (R=methyl) and orthopropionate (R=ethyl). The treatment is conviently effected by heating the ester of Formula II with an excess of the orthoalkane ester, the latter being used as solvent as well as reactant. Conduct of the treatment in particular instances is described in the Examples, hereinafter.

Compounds of Formula II are prepared by reduction of the corresponding nitrophenyl compounds of the formula:

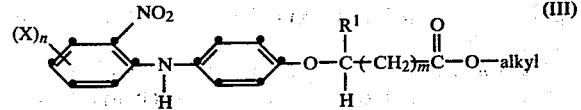

The reduction is conveniently effected by treatment of a solution of the nitro compound in an inert solvent such as tetrahydrofuran with hydrogen under pressure in the presence of a catalyst, such as charcoal impregnated with 10%w of palladium, using a suitable apparatus, such as a Parr shaker. Use of this method, too, in particular instances is described in the Examples.

The nitro compounds of Formula III, as a general class, and methods for preparing them, are described in U.S. Pat. No. 4,259,105. As described in the patent, two general methods can be used to prepare compounds of Formula III.

(1) Treatment of a phenol

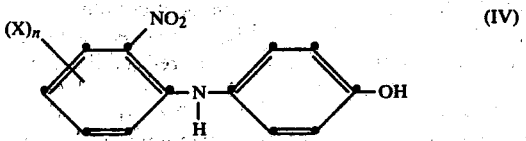

with a haloalkanoic acid or ester

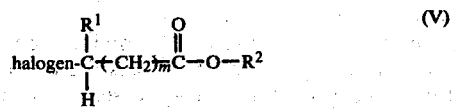

and (2) Treatment of a halide

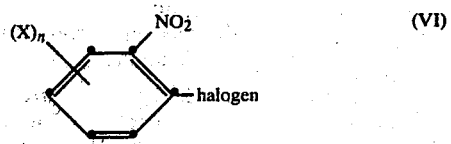

with an amine

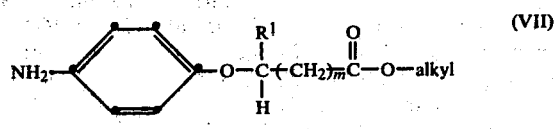

Techniques by which the reaction of the two materials can be conducted are described in the patent and are illustrated in particular instances in the Examples hereinafter.

Typical precursors to the phenols, halides and amines, and their preparation, are described in the patent and their preparation in particular instances is described in the Examples hereinafter.

Generally, the phenols (Formula IV) are prepared by effecting reaction between a halide

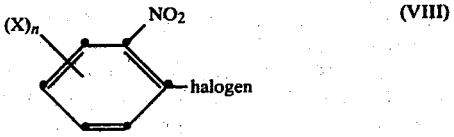

and p-aminophenol

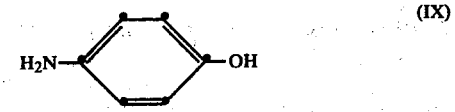

The amine precursors (Formula VII) are prepared by effecting reaction between 4-nitrophenol and an alkyl ester of a haloalkanoic acid (Formula V), in a solvent and in the presence of an alkaline condensing agent, such as potassium carbonate, and then catalytically reducing them with hydrogen to form the corresponding amine.

Preparation of the precursor wherein $R^1$=methoxymethyl is described in Example 10, hereinafter.

In the case where m=2, an alternate method of preparing the precursor (Formula II) is illustrated in Example 12, hereinafter: the alkenoic acid counterpart is first prepared and catalytically hydrogenated to both saturate the olefinic double bond and reduce the nitro moiety to the amino moiety.

Conversion of an acid ($R^2$=H) to an ester ($R^2$=alkyl) and vice versa is effected by conventional methods, illustrated in the Examples, hereinafter.

The salts of the subclass of the compounds of Formula I wherein $R^2$ is hydrogen are prepared by conventional methods.

Synthesis and isolation of individual compounds of Formula I in particular instances are described in the following examples. In each case, the identity of the product, and of any intermediate involved, was confirmed by appropriate chemical and spectral analyses.

EXAMPLE 1

Ethyl 2-(4-(5-(trifluoromethyl)benzimidazol-1-yl)phenoxy)-propionate (1)

A mixture of 225.5 g of 4-chloro-3-nitrobenzotrifluoride and 109 g of p-aminophenol in 500 ml of isopropyl alcohol was refluxed for 8 hours. Then 101 g of triethylamine was added, the mixture was refluxed for 2.5 hours, then concentrated to dryness. The residue was treated with 1000 ml of ether. The ethereal phase was separated, washed with water and diluted with 600 ml of hexane. The resulting mixture was filtered through silica gel and the filtrate was concentrated to give 4'-hydroxy-2-nitro-4-(trifluoromethyl)diphenylamine (1A), as a red solid, m.p.: 130°–133° C.

A mixture of 29.8 g of 1A, 18.4 g of ethyl 2-bromopropionate, 14 g of anhydrous potassium carbonate and 300 ml of 2-butanone was refluxed for 6 hours, poured into water, and the resulting mixture was extracted with ether. The extract was dried (MgSO$_4$), filtered and concentrated. Recrystallization of the residue from ether/hexane gave ethyl 2-(4-(2-nitro-4-(trifluoromethyl)phenylamino)phenoxy)propionate (1B), as a crystalline solid, m.p.: 61°–63° C.

1B, in tetrahydrofuran, was treated with hydrogen (40 psi pressure in a Parr-shaker, 10% palladium-on-carbon catalyst), to give ethyl 2-(4-(2-amino-4-(trifluoromethyl)phenylamino)phenoxy)propionate (1C), as a solid, m.p.: 78° C.

5.3 g of 1C was dissolved in 50 ml of triethyl orthoformate, the solution was refluxed for 1 hour, then concentrated under reduced pressure. The residue, an oil, was chromatographed over silica gel, using as eluent a 2:15:33 v/v/v mixture of tetrahydrofuran, ethyl acetate and hexane (hereinafter, Solvent A), to give 1, as a viscous liquid.

1B also was prepared by an alternate method, as follows:

A mixture of 28 g of 4-nitrophenol, 36 g of ethyl 2-bromopropionate, 27.6 g of potassium carbonate and 500 ml of butanone was stirred and refluxed for 17 hours. The resulting mixture was diluted with 500 ml of water and extracted with ether. The extract was concentrated in a rotary evaporator and the residue was recrystallized from ether-hexane to give ethyl 2-(4-nitrophenoxy)ropionate (1D), as a yellow solid, m.p.: 55°–56° C.

Hydrogenation of 1D (as described in preparation of 1C) gave ethyl 2-(4-aminophenoxy)propionte (1E), as a viscous oil.

A solution of 209 g of 1E, 111 g of triethylamine and 225.5 g of 4-chloro-3-nitrobenzotrifluoride in 600 ml of 2-butanone was refluxed for 24 hours, then concentrated in a rotary evaporator. The oily residue was dissolved in 1200 ml of ether; the solution was washed with water, dried (MgSO$_4$) and concentrated. Purification by silica gel chromatography (eluent: Solvent A) gave 1B.

EXAMPLE 2

2-(4-(5-(trifluoromethyl)benzimidazol-1-yl)phenoxy)-propionic acid (2)

A mixture of 3.7 g of 1, 0.39 g of sodium hydroxide and 50 ml of ethanol was refluxed for two hours, then it was cooled to room temperature, acidified with hydrochloric acid and extracted with ether. Concentration of the ether extract gave 2, as a white solid, m.p.: 181°–182° C.

EXAMPLES 3 and 4

Ethyl 2-(4-(2-methyl-5-(trifluoromethyl)benzimidazol-1-yl)phenoxy)propionate (3). Ethyl 2-(4-(2-ethyl-5-(trifluoromethyl)benzimidazol-1-yl)phenoxy)propionate (4)

3 was prepared, as an oil, from 1C and triethyl orthoacetate, and 4 was prepared, as a solid, m.p.: 66°–68° C., from 1C and triethyl orthopropionate by the procedures described in Example 1.

EXAMPLE 5

2-(4-(2-methyl-5-(trifluoromethyl)benzimidazol-1-yl)phenoxy)propionic acid (5)

5 was prepared, as a solid, m.p.: 107° C., from 3 by the procedure shown in the last step of the procedure described in Example 1.

EXAMPLE 6

Ethyl 2-(4-(2-methyl-5-(trifluoromethyl)benzimidazol-1-yl)phenoxy)butyrate (6)

A mixture of 14.9 g of 1A, 14.8 g of ethyl 2-bromobutyrate, 18.8 g of potassium carbonate and 150 ml of butanone was stirred and refluxed for 8 hours. The mixture then was diluted with water, acidified with hydrochloric acid and extracted with ether. The ether extract was dried (MgSO$_4$), filtered and concentrated in a rotary evaporator to give ethyl 2-(4-(2-nitro-4-(trifluoromethyl)phenylamino)phenoxy)butyrate (6A), as a viscous oil.

Hydrogenation of 6A as described in Example 1 gave ethyl 2-(4-(2-amino-4-(trifluoromethyl)phenylamino)-phenoxy)-butyrate (6B), as a viscous oil.

A solution of 7 g of 6B in 50 ml of triethyl orthoacetate was heated at 140° C. for 2 hours. The resulting mixture was cooled to room temperature, absorbed on silica gel and chromatographed, using the eluent described in Example 1, to give 6, as a viscous oil.

EXAMPLE 7

Ethyl 2-(4-(5-trifluoromethyl)benzimidazol-1-yl)phenoxy)butyrate (7)

7 was prepared, as an oil, from 6B and triethyl orthoformate, by the procedure described for the preparation of 6 from 6B.

EXAMPLE 8

2-(4-(2-methyl-5-(trifluoromethyl)benzimidazol-1-yl)phenoxy)butyric acid (8)

A mixture of 4.0 g of 6 and 0.4 g of sodium hydroxide in 50 ml of 50% ethanol was refluxed for 45 minutes, then concentrated to dryness. The residue was mixed with water, the mixture was acidified with hydrochloric acid and extracted with ether. The ether was evaporated from the extract and the residue was recrystallized from ether-hexane to give 8, as a white solid, m.p.: 98° C.

EXAMPLE 9

2-(4-(5-(trifluoromethyl)benzimidazol-1-yl)phenoxy)butyric acid (9)

9 was prepared, as a solid, m.p.: 214°–215° C., from 7, by the procedure described in Example 8.

EXAMPLE 10

Methyl 2-(4-(2-methyl-5-(trifluoromethyl)benzimidazol-1-yl)phenoxy)-3-methoxypropionate (10)

480 g of mercuric acetate was added to a solution of 139 g of methyl acrylate in 170 ml of methanol. The resulting mixture was stirred for 3 days at room temperature. To the mixture, cooled by an ice bath, a solution of 100 g of potassium bromide in 600 ml of water was added. A heavy oil formed, was separated from the mixture and was extracted with chloroform. The extract was washed with water, dried (MgSO$_4$) and filtered. The filtrate was heated to 60° C. and 36.9 g of bromine was added, drop-by-drop over a 2-hour period. The resulting mixture was cooled to 5° C. and concentrated in a rotary evaporator. The liquid residue was distilled to give methyl 2-bromo-3-methoxypropionate (10A), b.p.: 69°–72° C. (3–5 Torr.).

A mixture of 69 g of 10A, and 104 g of 1A, 45 g of potassium carbonate and 1000 ml of 2-butanone was stirred and refluxed for 3 days. The product, methyl 2-(4-(2-nitro-4-(trifluoromethyl)phenylamino)phenoxy)-3-methoxypropionate (10B), was obtained as a solid, m.p.: 57° C., by procedures described for the isolation of 1B.

A solution of 17 g of 10B in 100 ml of tetrahydrofuran was treated with hydrogen (40 psi hydrogen pressure, Parr-shaker, 10% palladium-on-charcoal catalyst) to give methyl 2-(4-(2-amino-4-(trifluoromethyl)phenylamino)phenoxy)-3-methoxypropionate (10C), as an oil.

A solution of 7 g of 10C in 25 ml of triethyl orthoacetate was refluxed for 4 hours. The resulting mixture was concentrated in a rotary evaporator and chromatographed over silica gel to give 10, as a viscous oil.

EXAMPLE 11

2-(4-(2-methyl-5-(trifluoromethyl)benzimidazol-1-yl)phenoxy)-3-methoxypropionic acid (11)

A solution of 4.5 g of 10 and 0.5 g of sodium hydroxide in 50 ml of aqueous methanol was refluxed for 2 hours. The resulting mixture was concentrated to dryness, the residue was acidified with dilute hydrochloric acid and extracted with ether. The extract was dried and concentrated. The residue was crystallized from ether-hexane to give 11, as a light tan crystalline solid, m.p.: 111°–112° C.

EXAMPLE 12

Ethyl 4-(4-(2-methyl-5-(trifluoromethyl)benzimidazol-1-yl)phenoxy)pentanoate (12)

A mixture of 56.2 g of trans-2-pentenoic acid and 100 g of N-bromosuccinimide in 1000 ml of carbon tetrachloride was stirred and refluxed for 24 hours. The resulting mixture was cooled to room temperature and filtered. The filtrate was concentrated to a volume of about 300 ml, cooled to room temperature and filtered to give trans-4-bromo-2-pentenoic acid, as a white crystalline solid (12A), m.p.: 78°–80° C.

25 g of hydrogen chloride was introduced into a solution of 139.2 g of 12A in 1000 ml of ethanol. The resulting mixture was refluxed for 36 hours, concentrated in a rotary evaporator, mixed with ice water and extracted with ether. The extract was washed to neutrality with aqueous sodium bicarbonate, dried (MgSO$_4$) and concentrated. The liquid residue was fractionally distilled to give ethyl 4-bromo-2-pentenoate (12B), as a colorless liquid, b.p.: 82° C. (1.8 Torr.).

A mixture of 71.5 g of 1A, 45.0 g of 12B, 33 g of potassium carbonate and 800 ml of 2-butanone was stirred and refluxed for 24 hours. The resulting mixture was divided in half. One half was concentrated to dryness, the residue was diluted with ether and shaken with 2.5% sodium hydroxide solution. The ether phase was separated, the ether was evaporated, and the residue was chromatographed over silica gel to give ethyl 4-(4-(2-nitro-4-(trifluoromethyl)phenylamino)phenoxy)-2-pentenoate (12C), as a viscous oil.

23 g of 12B and 16.8 g of potassium carbonate were added to the second half of the above mixture, and the resulting mixture was refluxed for 8 hours. The mixture was concentrated to dryness, the residue was mixed with ether and water, warmed, then cooled to room temperature and acidified with hydrochloric acid. The ether phase was separated, concentrated and chromatographed over silica gel to give 4-(4-(2-nitro-4-(trifluoromethyl)phenylamino)phenoxy)-2-pentenoic acid (12D), as a viscous oil.

12D, in solution in tetrahydrofuran, was placed on a Parr shaker and treated with hydrogen (40 psi hydrogen pressure, Parr shaker, 10% palladium-on-charcoal catalyst) to give 4-(4-(2-amino-4-(trifluoromethyl)phenylamino)phenoxy)pentanoic acid (12E), as an oil.

A solution of 3.1 g of 12E in 50 ml of triethyl orthoacetate was refluxed for 2 hours. The resulting mixture was concentrated in a rotary evaporator and the residue was chromatographed over silica gel to give 12, as a viscous oil.

EXAMPLE 13

4-(4-(2-methyl-5-(trifluoromethyl)benzimidazol-1-yl)phenoxy)pentanoic acid (13)

A solution of 2.4 g of 12 and 0.25 g of sodium hydroxide in 50 ml of aqueous ethanol was refluxed for one hour, and extracted with ether. The extract was dried and concentrated. The residue was crystallized from ether-hexane to give 13, as a white solid, m.p.: 67°–68° C.

Compounds of Formula I have been found to affect the growth of plants adversely, and therefore to be useful for controlling the growth of unwanted plants. Individually, the compounds differ one from another in their spectrum and level of phytotoxicity—some being more toxic to broadleaved plants than to grasses, others vice versa; some being nonactive when applied to the soil prior to emergence of the sprouting plants than when applied to the foliage of the growing plant, some vice versa.

Accordingly, the invention includes a method of controlling the growth of unwanted plants which comprises applying to the locus an effective amount of a compund of Formula I. Likewise, the invention includes plant growth control compositions comprising an inert carrier or a surface-active agent, or both a carrier and a surface-active agent, and, as active ingredient at least one compound of Formula I.

The term "carrier" as used herein means an inert solid or fluid material, which may be inorganic or organic and of synthetic or natural origin, with which the active compound is mixed or formulated to facilitate its application to the plant, seed, soil or other object to be treated, or its storage transport or handling.

Suitable solid carriers are natural and synthetic clays and silicates, for example, natural silicas such as diatomaceous earth; magnesium silicates, for example, talcs, magnesium aluminum silicates, for example, attapulgites and vermiculites; alumium silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example coumarone resins, polyvinyl chloride and styrene polymers and copolymers; bitumen, waxes such as, for example, beeswax, paraffin wax, and chlorinated minerals waxes; and solid fertilizers, for example, superphosphates.

Examples of suitable fluid carriers are water, dimethyl sulfoxide, alcohols, such as, for example, methanol, isopropyl alcohol, glycols; ketones such as for example, acetone, methyl ethyl ketone, methyl isobutyl ketone, isophorone and cyclohexanone; ethers such as, for example, cellosolves; aromatic hydrocarbons such as, for example, benzene, toluene and xylene; petroleum fractions such as, for example, herosene, light mineral oils; chlorinated hydrocarbons, such as, for example, carbon tetrachloride, perchloroethylene, trichloroethane, including liquefied normall vaporous gaseous compounds. Mixtures of different liquids are often suitable. The surface-active agent may be an emulsifying agent or a dispersing agent or a wetting agent; it may be nonionic or ionic any of the surface-active agents usually applied in formulating herbicides or insecticides may be used. Examples of suitable surface-active agents are sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil and sodium alkyl-aryl sulfonates such as sodium dodecylbenzene sulfonate; and polymers of ethylene oxide and copolymers of ethylene oxide and propylene oxides.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, 15% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½–10% by weight of toxicant. Granules are usually prepared to have a size between 10 and 100 BS mesh (1.676–0.152 mm), and may be manufactured by agglomeration or impregnation techniques. Generally, granules will contain ½–25% by weight toxicant and 0–1% by weight of additives such as stabilizers, slow release modifiers and binding agents. Emulsifiable concentrates usually contain, in addition to the solvent and, when necessary, cosolvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, nonsedimenting flowable product and usually contain 10–75% weight toxicant, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also like within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal properties.

Protection of a locus or area from unwanted plants is effected by applying a compound of Formula I, ordinarily in a composition of one of the aforementioned types, to the soil in which seeds of the unwanted plants are present, or to the foliage of the plants. The active compound, of course, is applied in an amount sufficient to exert the desired action.

The amount of compound of the invention to be used in controlling undesired plants will naturally depend on the condition of the plants, the degree of activity desired, the formulation used, the mode of application, the climate, the season of the year, and other variables. Recommendations as to precise amounts are, therefore, not possible. In general, howevr, application to the locus to be protected of from 0.1 to 10.0 kilograms per hectare of the compound of Formula I will be satisfactory.

EXAMPLES OF HERBICIDAL ACTIVITY

In the following examples, the species of plants that were tested were:
Barnyardgrass (watergrass)—*Echinochloa crus-galli*
Large crabgrass—*Digitaria sanguinalis*
Downy brome—*Bromus tectorum*
Yellow foxtail—*Setaria lutescens*
Redroot pigweed—*Amaranthus retroflexus*
Sicklepod—*Cassia obtusifolia*
Velvetleaf—*Abutilon theophrasti*
Garden cress—*Lepidium sativum*
Johnsongrass—*Sorghum halepense*

Test Procedures

The preemergence (soil) herbicidal activity of compounds of the invention was evaluated by planting seeds of barnyardgrass, garden cress, downy brome, velvetleaf, yellow foxtail, and sicklepod in test tubes, nominally measuring 25×200 millimeters, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 milligram of the test compound per each tube containing the seeds of the other plants. The dosages were approximately 22 and 2.2 pounds of test compound per acre, respectively. The seeds were planted on top of the treated soil and covered with about 1.5 cubic centimeters of untreated soil. The planted soil was held under controlled conditions and temperature, moisture, and light for 9 to 10 days. The amounts of germination and growth in each tube were evaluated on a 0 to 9 scale, the numeric ratings having the following meanings:

| Rating | Meaning |
|---|---|
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3–4 | Observable damage |
| 1–2 | Plant slightly affected, possibly by the chemical, possibly due to biological variability |
| 0 | No visible effect |

The postemergence (foliar) herbicidal activity of compounds of the invention was evaluated by spraying 10-day-old large downy brome plants in some cases, 6-day-old Johnsongrass plants in other cases, 9-day-old velvetleaf plants, 9-day-old yellow foxtail plants and 9-day-old sicklepod plants to runoff with a liquid formulation of the test compound. The crabgrass and pigweed plants were sprayed with 2.4 milliliters of a 0.25% solution (about ten pounds of the test compound per acre), and other plants were sprayed with 2.4 milliliters of a 0.025% solution (about one pound of the test compound per acre). The sprayed plants were held under controlled conditions of temperature, moisture and light for 7 to 8 days and the effect of the test compound was then evaluated visually, the results being rated on the 0 to 9 scale described above.

Results of the preemergence and postemergence herbicidal activity tests conducted on the compounds of the invention are set forth in Table I.

TABLE I
HERBICIDAL ACTIVITY

| Compound | Preemergence | | | | | | Postemergence | | | | | |
|---|---|---|---|---|---|---|---|---|---|---|---|---|
| | Barnyard-grass | Garden cress | Downy brome | Velvet-leaf | Yellow foxtail | Sickle-pod | Crab-grass | Pig-weed | Johnson-grass | Velvet-leaf | Yellow foxtail | Sickle-pod |
| 1 | 6 | 6 | 0 | 0 | 0 | 0 | 9 | 8 | 7 | 2 | 4 | 5 |
| 2 | 8 | 8 | 6 | 0 | 0 | 2 | 7 | 7 | 7 | 2 | 5 | 5 |
| 3 | 7 | 4 | 0 | 2 | 0 | 0 | 9 | 9 | 9 | 2 | 8 | 2 |
| 4 | 0 | 4 | 0 | 0 | 0 | 0 | 3 | 6 | 0 | 3 | 0 | 2 |
| 5 | 9 | 6 | 5 | 3 | 5 | 2 | 8 | 7 | 8 | 2 | 6 | 1 |
| 6 | 0 | 0 | 0 | 0 | 0 | 0 | 8 | 3 | 7 | 0 | 2 | 2 |
| 7 | 0 | 5 | 0 | 0 | 0 | 0 | 7 | 6 | 3 | 2 | 2 | 2 |
| 8 | 7 | 7 | 0 | 0 | 0 | 0 | 8 | 4 | 7 | 2 | 2 | 2 |
| 9 | 7 | 8 | 0 | 0 | 0 | 0 | 1 | 2 | 1 | 0 | 0 | 2 |
| 10 | 4 | 4 | 2 | 0 | 2 | 0 | 4 | 9 | 2 | 2 | 2 | 0 |
| 11 | 0 | 2 | — | 0 | 0 | 0 | 3 | 5 | 0 | 3 | 0 | 0 |
| 12 | 0 | 6 | 0 | 0 | 0 | 0 | 2 | 4 | 0 | 0 | 0 | 0 |
| 13 | 0 | 0 | 0 | 0 | 0 | 0 | 5 | 9 | 4 | 0 | 0 | 0 |

I claim:
1. A compound of the formula:

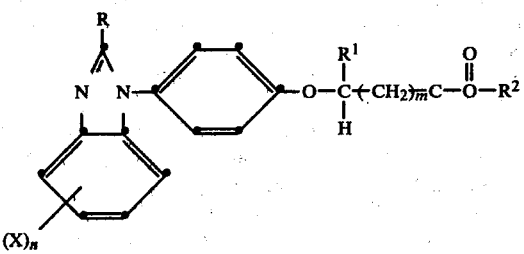

wherein n is 1 and X is trifluoromethyl, R is hydrogen, methyl or ethyl, $R^1$ is methyl, ethyl or methoxymethyl; m is 0, 1 or 2; and $R^2$ is hydrogen, alkyl of from one to four carbon atoms, or when $R^2$ is hydrogen, an alkali metal, or ammonium ($N(R^3)_3$), salt wherein each $R^3$ is hydrogen or alkyl of from one to six carbon atoms.

2. A compound according to claim 1 wherein n is one, X represents the trifluoromethyl moiety, bonded to the ring at the 5-position, R and $R^1$ each represents methyl, m is 0, and $R^2$ represents hydrogen, methyl or ethyl.

3. A composition adapted to control of unwanted plants, comprising an effective amount of a compound of claim 1 together with a carrier, a surface-active agent, or both.

4. A composition according to claim 3 wherein the compound of claim 1 is one wherein the trifluoromethyl moiety is bonded to the ring at the 5-position, R and $R^1$ each represents methyl, m is 0 and $R^2$ represent hydrogen, methyl or ethyl.

5. A method for controlling growth of unwanted plants at a locus which comprises applying to that locus an effective amount of a compound of claim 1.

6. A method for controlling growth of unwanted plants at a locus which comprises applying to that locus an effective amount of a compound of claim 2.

* * * * *